United States Patent
Li et al.

(10) Patent No.: US 12,325,700 B2
(45) Date of Patent: Jun. 10, 2025

(54) CRYSTAL FORM S4 OF THE PLK4 INHIBITOR (1R,2S)-(E)-2-(3-(4-((CIS-2,6-DIMETHYL MORPHOLINO)METHYL)STYRYL)-1 H-IMIDAZOL-6-YL)-5'-METHOXYSPIRO [CYCLOPROPANE-1,3'-INDOLIN]-2'-ONE FUMARATE

(71) Applicant: UNIVERSITY HEALTH NETWORK, Toronto (CA)

(72) Inventors: Sze-Wan Li, Toronto (CA); Mark Robert Bray, Oakville (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 834 days.

(21) Appl. No.: 17/605,108

(22) PCT Filed: Apr. 23, 2020

(86) PCT No.: PCT/CA2020/050535
§ 371 (c)(1),
(2) Date: Oct. 20, 2021

(87) PCT Pub. No.: WO2020/215155
PCT Pub. Date: Oct. 29, 2020

(65) Prior Publication Data
US 2022/0204494 A1 Jun. 30, 2022

Related U.S. Application Data

(60) Provisional application No. 62/837,858, filed on Apr. 24, 2019.

(51) Int. Cl.
*C07D 413/14* (2006.01)

(52) U.S. Cl.
CPC ........ *C07D 413/14* (2013.01); *C07B 2200/13* (2013.01)

(58) Field of Classification Search
CPC C07D 413/14; C07D 403/04; C07B 2200/13; A61K 31/5377; A61P 35/00
(Continued)

(56) References Cited

U.S. PATENT DOCUMENTS 7,205,328 B2  4/2007  He et al.
7,511,059 B2  3/2009  Schulze et al.
(Continued)

FOREIGN PATENT DOCUMENTS

EP  3057965 B1  1/2019
JP  2008-529985 A  8/2008
(Continued)

OTHER PUBLICATIONS

Aaltonen et al., Solid form screening—a review. Eur J Pharm Biopharm. Jan. 2009;71(1):23-37.
(Continued)

*Primary Examiner* — Taylor V Oh
(74) *Attorney, Agent, or Firm* — McCarter & English, LLP; Steven G. Davis; Wei Song (57) ABSTRACT

Disclosed is Crystal Form S4 of a fumarate salt of compound (I) represented by the following structural formula: (I) The molar ratio between compound (I) and fumaric acid is 1.0:1:0. Crystal Form S4, 5 characterized by an X-ray powder diffraction pattern which comprises peaks at 6.6°, 9.8°, 16.3°, 21.1°, 28.7°, and 30.2°±0.2 in 2θ.

(Continued)

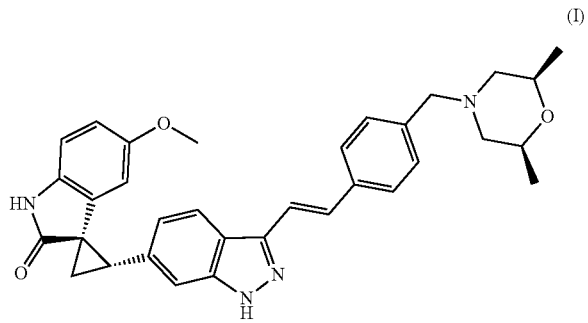

25 Claims, 3 Drawing Sheets (58) Field of Classification Search
USPC .................................................. 544/140
See application file for complete search history.

(56) References Cited

U.S. PATENT DOCUMENTS

| | | |
|---|---|---|
| 8,263,596 B2 | 9/2012 | Sampson et al. |
| 8,318,727 B2 | 11/2012 | Cao et al. |
| 8,481,525 B2 | 7/2013 | Sampson et al. |
| 8,481,533 B2 | 7/2013 | Sampson et al. |
| 8,765,748 B2 | 7/2014 | Pauls et al. |
| 8,921,545 B2 | 12/2014 | Cumming et al. |
| 8,933,070 B2 | 1/2015 | Pan et al. |
| 8,999,968 B2 | 4/2015 | Sampson et al. |
| 9,139,563 B2 | 9/2015 | Sampson et al. |
| 9,402,828 B2 | 8/2016 | Pan et al. |
| 9,884,855 B2 | 2/2018 | Sampson et al. |
| 9,907,800 B2 | 3/2018 | Sampson et al. |
| 10,358,436 B2 | 7/2019 | Sampson et al. |
| 10,392,374 B2 | 8/2019 | Sampson et al. |
| RE47,731 E | 11/2019 | Sampson et al. |
| 10,472,353 B2 | 11/2019 | Sampson et al. |
| 10,919,886 B2 | 2/2021 | Sampson et al. |
| 2011/0263598 A1 | 10/2011 | Sampson et al. |
| 2015/0133677 A1 | 5/2015 | Cumming et al. |
| 2016/0045511 A1 | 2/2016 | Sampson et al. |
| 2016/0250220 A1 | 9/2016 | Hedley et al. |
| 2021/0269428 A1 | 9/2021 | Sampson et al. |

FOREIGN PATENT DOCUMENTS

| | | |
|---|---|---|
| JP | 2010-540463 A | 12/2010 |
| JP | 2011-506494 A | 3/2011 |
| JP | 2012-522729 A | 9/2012 |
| JP | 2012-525345 A | 10/2012 |
| JP | 2014-511336 A | 5/2014 |
| WO | 2007/110559 A1 | 10/2007 |
| WO | 2010/115279 A1 | 10/2010 |
| WO | 2010/125004 A1 | 11/2010 |
| WO | 2011/123946 A1 | 10/2011 |
| WO | 2011/123947 A1 | 10/2011 |
| WO | 2012/000103 A1 | 1/2012 |
| WO | 2012/048411 A1 | 4/2012 |
| WO | 2012/121764 A1 | 9/2012 |
| WO | 2013/053051 A1 | 4/2013 |
| WO | 2015/054781 A1 | 4/2015 |

OTHER PUBLICATIONS

Ashizawa et al., Polymorphism and crystallization of pharmaceutical drugs. pp. 3-16, Sep. 20, 2002.
Berge et al., Pharmaceutical Salts. Journal of Pharmaceutical Sciences. 1977;66(1):1-19.
Brittain, Polymorphism in Pharmaceutical Solids, vol. 95. Marcel Dekker, Inc., New York. 235 pages (1999).
Byrn et al., Pharmaceutical solids: a strategic approach to regulatory considerations. Pharm Res. Jul. 1995;12(7):945-54.
Caira, Crystalline Polymorphism of Organic Compounds. Topics in Current Chemistry, Springer Verlag, Berlin. vol. 198, pp. 163-208 (1998).
CAS RN 1247005-59-9, Spiro[cyclopropane-1,3'-[3H]indol]-2'[1'H]-one, 2-[3-[(1E)-2-[4-[(2S,6S)-2,6-dimethyl-4-morpholinyl]methyl]phenyl]ethenyl]-1H-indazol-6-yl'-5'-methoxy-, (1R,2S)-(CA Index Name). 1 page, Oct. 26, 2010.
Chouzaigaku: Kiso to Ohyou (Pharmacy: Basics and Application), pp. 142-145, Sep. 20, 1977.
Gu et al., Grouping solvents by statistical analysis of solvent property parameters: implication to polymorph screening. Int J Pharm. Sep. 28, 2004;283(1-2):117-25.
Ivanisevic et al., Uses of X-Ray Powder Diffraction In the Pharmaceutical Industry. Pharmaceutical Sciences Encyclopedia: Drug Discovery, Development, and Manufacturing. John Wiley & Sons, Inc., Shayne C. Gad (Ed.). pp. 1-42, (2010).
Mason et al., Functional characterization of CFI-400945, a Polo-like kinase 4 inhibitor, as a potential anticancer agent. Cancer Cell. Aug. 11, 2014;26(2):163-76.
Morissette et al., High-throughput crystallization: polymorphs, salts, co-crystals and solvates of pharmaceutical solids. Adv Drug Deliv Rev. Feb. 23, 2004;56(3):275-300.
Paulekuhn et al., Trends in active pharmaceutical ingredient salt selection based on analysis of the Orange Book database. J Med Chem. Dec. 27, 2007;50(26):6665-72.
Ribet et al., Conformational analysis and crystal structure of {[1-(3-chloro-4-fluorobenzoyl)-4-fluoropiperidin-4yl]methyl}[(5-methylpyridin-2-yl)methyl]amine, fumaric acid salt. Spectrochim Acta A Mol Biomol Spectrosc. Nov. 2005;62(1-3):353-63.
Sampson et al., The discovery of Polo-like kinase 4 inhibitors: design and optimization of spiro[cyclopropane-1,3?'[3H]indol]-2'(1'H).ones as orally bioavailable antitumor agents. J Med Chem. Jan. 8, 2015;58 (1):130-46.
Sampson et al., The discovery of Polo-like kinase 4 inhibitors: identification of (1R,2S).2-(3-((E).4-(((cis).2,6-dimethylmorpholino)methyl)styryl). 1H.indazol-6-yl)-5?'-methoxyspiro[cyclopropane-1,3?'-indolin]-2?'-one (CFI-400945) as a potent, orally active antitumor agent. J Med Chem. Jan. 8, 2015;58(1):147-69.
Shin-Seizaigaku (New Pharmaceuticals) pp. 102-103, 232-233, Apr. 25, 1984.
Shin-Yakuzaigaku Souron (New General Review of Pharmaceuticals) p. 111, Apr. 25, 1987.
U.S. Pharmacopeia, X-Ray Diffraction. Chapter 941. Retrieved online at: http://www.pharmacopeia.cn/v29240/usp29nf24s0c941.html. 4 pages (2013).
Zoku-JikkennKagaku Koza (Experimental Chemistry, second series) pp. 159-178, 186-187, Jan. 25, 1967.
International Search Report and Written Opinion for Application No. PCT/CA2020/050535, dated Jul. 6, 2020, 11 pages.
Japanese Office Action for Application No. 2016-524077, dated Jul. 5, 2018. 9 pages.
Augsburger et al., Pharmaceutical Dosage Forms: Tablets, 3rd Edition, vol. 2. Chapter 2, pp. 62-66, Dec. 31, 2008.

CRYSTAL FORM S4 OF THE PLK4 INHIBITOR (1R,2S)-(E)-2-(3-(4-((CIS-2,6-DIMETHYL MORPHOLINO)METHYL)STYRYL)-1 H-IMIDAZOL-6-YL)-5'-METHOXYSPIRO [CYCLOPROPANE-1,3'-INDOLIN]-2'-ONE FUMARATE

CROSS-REFERENCE TO RELATED APPLICATIONS

This application is a U.S. national stage filing, under 35 U.S.C. § 371(c), of International Application No. PCT/CA2020/050535, filed Apr. 23, 2020, which claims priority to U.S. Provisional Application No. 62/837,858, filed Apr. 24, 2019. The entire contents of the aforementioned application are incorporated herein by reference.

BACKGROUND

The polo-like kinase (PLK) family of serine/threonine kinases comprises at least four known members: PLK1, PLK2 (also known as Snk), PLK3 (also known as Fnk or Prk) and PLK4 (also known as Sak). Agents which inhibit PLK4 have the potential to treat cancer. A number of potent PLK4 inhibitors are disclosed in U.S. Pat. Nos. 8,263,596; 8,481,525; and 8,481,533 (the entire teachings of which are incorporated herein by reference). The structure of one inhibitor disclosed in these patents is shown below as compound (I):

(I)

There is a need for salt forms of this compound that are crystalline and otherwise have physical properties that are amenable to manufacturing-scale production. There is also a need for pharmaceutical formulations in which this drug candidate is stable and is effectively delivered to the patient.

In this context, U.S. Pat. No. 9,884,855 discloses several crystal forms of the 1:1 fumarate salt of compound (I), including form D, as potential anticancer drug candidates. The entire teachings of U.S. Pat. No. 9,884,855 are incorporated herein by reference. "1:1" refers to the molar ratio between fumaric acid and compound (I).

SUMMARY OF THE INVENTION

Form D was selected for scale-up because, as disclosed in U.S. Pat. No. 9,884,855, it can be produced in a crystalline state, has low hygroscopicity, and is an effective anti-cancer agent with good solubility and favorable pharmacokinetic properties. However, it was later found that the production of form D in a large scale manufacturing process resulted in a mixture of different crystalline forms (see Example 3).

A new crystal form, referred to as "S4", has now been discovered that has the beneficial properties of form D (e.g., has low hygroscopicity and good solubility, and possesses superior pharmacokinetic properties (see Examples 6 and 7). More importantly, it overcomes the problems associated with form D. Specifically, form S4 can be prepared in a good yield with high purity and is amenable to scale-up (see Examples 4 and 5).

Consequently, the present disclosure provides a fumarate salt of compound (I), wherein the molar ratio between compound (I) and fumaric acid being 1:1, and the fumarate salt comprises (is) crystal form S4, characterized by an X-ray powder diffraction (XRPD) pattern which comprises peaks at 6.6°, 9.8°, 16.3°, 21.1°, 28.7°, and 30.2°±0.2 in 2θ.

The present disclosure also provides a pharmaceutical composition comprising crystal form S4 of the 1:1 fumaric acid salt of compound (I), and a pharmaceutically acceptable carrier or diluent.

The present disclosure also provides a method of preparing crystal form S4 of the 1:1 fumarate acid salt of compound (I). The method comprises dissolving fumaric acid and compound (I) in a dissolution solvent comprising 2-butanone, water, and ethanol to form a crystallization solution, and then precipitating the crystal form S4 from the crystallization solution, wherein the molar ratio between compound (I) and fumaric acid in the dissolution solvent is about 1:1 to about 1:1.3; and the molar ratio between compound (I) and fumaric acid in the fumarate salt of compound (I) is 1:1. In one aspect, the dissolution of fumaric acid and compound (I) occurs at an elevated temperature, and the precipitation of the crystal form S4 from the crystallization solution is by way of cooling and/or adding methylcyclohexane with cooling.

Also provided is a method of treating cancer. The method comprises administering to a subject with cancer an effective amount of form S4 of the 1:1 fumarate acid salt of compound (I).

Also provided is the use of crystal form S4 of the fumarate salt of compound (I) for the manufacture of a medicament for treating cancer.

Also provided is the crystal form S4 of the fumarate acid salt of compound (I) for use in treating cancer.

DETAILED DESCRIPTION OF THE INVENTION

The present disclosure provides a novel crystal form S4 of 1:1 fumurate salt of compound (I) and the corresponding pharmaceutical compositions. The present disclosure also provides a novel method of preparing crystal form S4 in a reproducible and scalable manner with a superior yield and purity. Additionally, the present disclosure provides a method of treating cancer.

Crystalline Forms of 1:1 Fumarate Salt of Compound (I)

In some embodiments, at least a particular percentage by weight of 1:1 fumarate salt of compound (I) is in a single crystal form. Particular weight percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a weight percentage range of 70%-75%, 75%-80%, 80%-85%, 85%-90%, 90%-95%, 95%-100%, 70-80%, 80-90%, 90-100%. For example, in one embodiment, at least 80% (e.g., at least 90% or 99%) by weight of the 1:1 compound (I) fumarate is in a single crystal form. It is to be understood that all values and ranges between these values and ranges are meant to be encompassed by the present disclosure.

As used herein, "crystalline" refers to a solid having a crystal structure wherein the individual molecules have a highly homogeneous regular locked-in chemical configuration. Crystalline 1:1 fumarate salt of compound (I) can be crystals of a single crystal form of 1:1 fumarate salt of compound (I), or a mixture of crystals of different single crystalline forms. A single crystal form means 1:1 fumarate salt of compound (I) as a single crystal or a plurality of crystals in which each crystal has the same crystal form.

When a particular percentage by weight of 1:1 fumarate salt of compound (I) is in a single crystal form, the remainder of the fumarate is some combination of amorphous fumarate, and/or one or more other crystal forms of 1:1 compound (I) fumarate excluding the single crystal form. When the crystalline 1:1 fumarate salt of compound (I) is defined as a specified percentage of one particular crystal form of 1:1 fumarate salt of compound (I), the remainder is made up of amorphous form and/or crystal forms other than the one or more particular forms that are specified. Examples of a single crystal form include form S4 of 1:1 compound (I) fumarate characterized by one or more properties as discussed herein.

In another embodiment, less than 30%, 25%, 20%, 10%, 9%, 8%, 7%, 6%, 5%, 4%, 3%, 2%, 1%, 0.5% by weight of the 1:1 fumarate salt of compound (I) is crystal form D. The amount of form S4 relative to form D in a sample can be assessed by preparing a series of mixtures of form S4 and form D with known weight ratios and obtaining an XRPD spectrum for each. The relative amounts of form S4 to form D in the sample is assessed by selecting one or more characteristic peaks of form S4 and form D and correlating their relative intensities in the sample XRPD to their relative intensities in the mixture XRPDs. The characteristic XRPD peaks for crystal form D is provided in Table 4 of U.S. Pat. No. 9,884,855.

1:1 fumarate salt of Compound (I) is at least 60%, 70%, 80%, 90%, 99% or 99.9% by weight pure relative to the other stereoisomers, i.e., the ratio of the weight of the stereoisomer over the weight of all the stereoisomers.

Preparation of 1:1 Fumarate Salt of Compound (I) Crystalline Form S4

A 1:1 fumarate salt of compound (I) solid form can be prepared, for example, by slow evaporation, slow cooling, and anti-solvent precipitation. The present disclosure provides a novel crystallization procedure to prepare crystal form S4 in a reproducible and scalable manner with an improved yield and purity.

As used herein, an "anti-solvent" refers to a solvent, in which 1:1 fumarate salt of compound (I) has a low solubility, causing the fumarate salt to precipitate out of a solution in the form of fine powders or crystals.

Alternatively, 1:1 fumarate salt of compound (I) can be recrystallized from a suitable solvent with or without the addition of seed crystals.

In one embodiment, the crystal form S4 of the 1:1 fumarate salt of compound (I) can be prepared by dissolving fumaric acid and compound (I) in a dissolution solvent comprising 2-butanone, water, and ethanol to form a crystallization solution, and then precipitating the S4 crystal form from the crystallization solution, wherein the molar ratio between compound (I) and fumaric acid in the dissolution solvent is about 1:1 to about 1:1.3; and the molar ratio between compound (I) and fumaric acid in the fumarate salt of compound (I) is 1:1. In one aspect of this embodiment, the dissolution of fumaric acid and compound (I) occurs at an elevated temperature, and the precipitation of the crystal form S4 from the crystallization solution is by way of cooling and/or adding methylcyclohexane with cooling.

In another embodiment, the crystal form S4 of the 1:1 fumarate salt of compound (I) is prepared by: (i) dissolving compound (I) in a mixture of 2-butanone and water at an elevated temperature to form a compound (I) solution; (ii) dissolving fumaric acid in ethanol at an elevated temperature to form a fumaric acid solution; (iii) adding the fumaric acid solution to the compound (I) solution at an elevated temperature to form the crystallization solution; (iv) optionally adding seed crystals at an elevated temperature to the crystallization solution; and (v) reducing the temperature of the crystallization solution to precipitate the S4 crystal form. In one aspect of this embodiment, the volume ratio between 2-butanone and water is between 80:20 and 98:2 (e.g. 90:10 and 98:2), and the volume ratios of 2-butanone/water to ethanol to methylcyclohexane are 6-7 to 4-5 to 11-22; the elevated temperature is between 45° C. and 55° C.; and the reduced temperature is between 20° C. and 30° C. In another aspect of this embodiment, the method further comprises adding methylcyclohexane at a reduced temperature to the crystallization solution to precipitate the S4 crystal form. In one specific aspect, the reduced temperature is between 20° C. and 30° C. In another specific aspect, the temperature of the crystallization solution is further reduced to precipitate the S4 crystal form. In a more specific aspect, the further reduced temperature is between 0° C. and 10° C.

Characterization of 1:1 Fumarate Salt of Compound (I) Single Crystal Form S4

Figure 1:
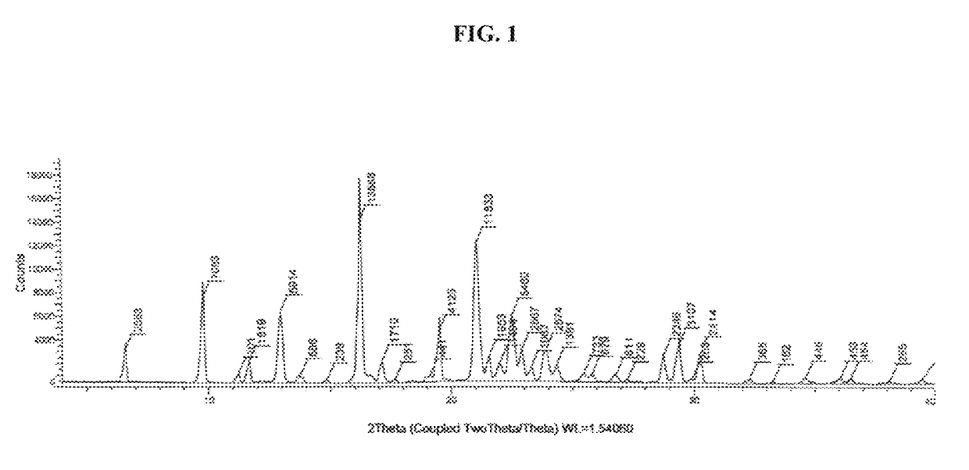
FIG. 1 depicts an X-ray powder diffraction pattern (XRPD) for crystal form S4 of 1:1 fumarate acid salt of compound (I) from a 100 g production.

In one embodiment, form S4 exhibits a unique XRPD pattern with sharp peaks corresponding to angular peak positions in 2θ and a flat baseline, indicative of a highly crystalline material (see FIG. 1). The XRPD pattern is obtained from a copper radiation source (CuKα; λ=1.54056 Å) operated at 40 V/30 mA. In one specific embodiment, form S4 is a single crystal form of 1:1 fumarate salt of compound (I), characterized by an X-ray powder diffraction pattern which comprises peaks at 6.6°, 9.8°, 16.3°, 21.1°, 28.7°, and 30.2°. In another specific embodiment, form S4 is characterized by an X-ray powder diffraction pattern which comprises peaks at 6.6°, 9.8°, 16.3°, 21.1°, 28.7°, 29.4°, and 30.2°. In another specific embodiment, form S4 is characterized by an X-ray powder diffraction pattern which comprises peaks at 6.6°, 9.8°, 13.0°, 16.3°, 19.5°, 21.1°, 22.5°, 28.7°, 29.4°, and 30.2°. In yet another specific embodiment, form S4 is characterized by an X-ray powder diffraction pattern which comprises peaks at 6.6°, 9.8°, 13.0°, 16.3°, 19.5°, 21.1°, 22.5°, 22.9°, 23.9°, 28.7°, 29.4°, and 30.2°. In yet another specific embodiment, form S4 is characterized by an X-ray powder diffraction pattern which comprises peaks at 6.6°, 9.8°, 11.6°, 13.0°, 16.3°, 17.1°, 19.5°, 21.1°, 21.5°, 22.0°, 22.5°, 22.9°, 23.9°, 24.3°, 28.7°, 29.4°, and 30.2°.

In yet another specific embodiment, form S4 is characterized by an X-ray powder diffraction pattern substantially similar to FIG. 1.

As used herein, an X-ray powder diffractogram is "substantially similar to that in [a particular] Figure" when at least 90%, such as at least 95%, at least 98%, or at least 99%, of the signals in the two diffractograms are the same ±0.2 in 2θ. In determining "similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance as discussed below.

It is well known in the crystallography art that, for any given crystal form, an angular peak position may vary slightly due to factors such as temperature variation, sample displacement, and the presence or absence of an internal standard. In the present disclosure, the variability of an angular peak position is ±0.2 in 2θ. In addition, the relative peak intensities for a given crystal form may vary due to differences in crystallite sizes and non-random crystallite orientations in sample preparation for XRPD analysis. It is well known in the art that this variability will account for the above factors without hindering the unequivocal identification of a crystal form.

Methods of Treatment

PLK4, as a member of the polo family of serine/threonine protein kinases, is known to be involved in cellular mitotic progression. Thus, a small molecule inhibitor of this enzyme can be a potential anticancer agent.

The present disclosure provides a method of treating a subject with a disease which can be ameliorated by inhibition of PLK4, such as treating cancer or inhibiting tumor growth, by administering to the subject an effective amount of form S4. As such, form S4 inhibits the growth of the tumor by inducing apoptosis of the tumor cells or by inhibiting proliferation of the tumor cells.

Specific cancers that can be treated by the disclosed method include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one specific embodiment, the cancer is lung cancer, breast cancer, colon cancer, neuroblastoma, prostate cancer, melanoma, glioblastoma multiforme, ovarian cancer, lymphoma, leukemia, osteosarcoma, germinoma, glioma, fibrosarcoma, gastrointestinal sarcoma, fibrous histiocytoma, round cell sarcoma, synovial sarcoma, cervical cancer, anogenital cancer, head and neck cancer, and oropharyngeal cancer. In one specific embodiment, the cancer is lung cancer, colon cancer, brain cancer, neuroblastoma, prostate cancer, melanoma, glioblastoma multiforme or ovarian cancer. In another specific embodiment, the cancer is lung cancer, breast cancer, colon cancer, brain cancer, neuroblastoma, prostate cancer, melanoma, glioblastoma multiform or ovarian cancer. In another specific embodiment, the cancer is lung cancer, breast cancer, and colon cancer. In yet another specific embodiment, the cancer is a breast cancer. In yet another specific embodiment, the cancer is a basal sub-type breast cancer or a luminal B sub-type breast cancer. In one embodiment, the basal sub-type breast cancer is ER (estrogen receptor), HER2 and PR (progesterone receptor) negative breast cancer. In yet another specific embodiment, the cancer is a triple negative breast cancer. The term "triple negative breast cancer" refers to a breast cancer that tests negative for hormones estrogen, progesterone, and HER2 under the ASCO/CAP Clinical Practice Guideline. In some embodiments, the triple negative breast cancer is unresectable or metastatic. In a particular embodiment, the method described above is used for treating a subject with pancreatic cancer, wherein the pancreatic cancer is adenocarcinoma. In another particular embodiment, the pancreatic cancer is hypoxic. In still another particular embodiment, the pancreatic cancer is non-hypoxic.

A soft tissue cancer can also be treated by the disclosed method. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma. The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

As used herein, "treating a subject with a cancer" includes achieving, partially or substantially, one or more of the following: arresting the growth of a cancer, reducing the extent of a cancer (e.g., reducing size of a tumor), inhibiting the growth rate of a cancer, ameliorating or improving a clinical symptom or indicator associated with the cancer (such as tissue or serum components) or increasing longevity of the subject; and reducing the likelihood of recurrence of the cancer.

As used herein, the term "reducing the likelihood of recurrence of a cancer" means inhibiting or delaying the return of a cancer at or near a primary site and/or at a secondary site after a period of remission. It also means that the cancer is less likely to return with treatment described herein than in its absence.

As used herein, the term "remission" refers to a state of cancer, wherein the clinical symptoms or indicators associated with a cancer have disappeared or cannot be detected, typically after the subject has been successfully treated with an anti-cancer therapy.

Generally, an effective amount of a compound of the disclosure varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present disclosure may be readily determined by one of ordinary skill by routine methods known in the art.

In one embodiment, an effective amount of 1:1 fumarate salt of compound (I) ranges from about 0.01 to about 1000 mg/kg body weight, alternatively about 0.05 to about 500 mg/kg body weight, alternatively about 0.1 to about 100 mg/kg body weight, alternatively about 0.1 to about 15 mg/kg body weight, alternatively about 1 to about 5 mg/kg body weight, and in another alternative, from about 2 to about 3 mg/kg body weight. The skilled artisan will appreciate that certain factors may influence the dosage required to effectively treat a subject suffering from cancer and these factors include, but are not limited to, the severity of the disease or disorder, previous treatments, the general health and/or age of the subject and other diseases present.

Moreover, a "treatment" regime of a subject with an effective amount of the fumarate salt of compound (I) of the present disclosure may consist of a single administration, or alternatively comprise a series of applications. For example, 1:1 fumarate salt of compound (I) may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present disclosure, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds of the present disclosure can be administered to a patient in a variety of forms depending on the selected route of administration, as will be understood by those skilled in the art. The compounds of the disclosure may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.
Pharmaceutical Compositions and Methods of Administration The 1:1 fumarate salt of compound (I) crystal form S4 disclosed herein can be suitably formulated into pharmaceutical compositions for administration to a subject. In one embodiment, the present disclosure provides a pharmaceutical composition comprising form S4 as described above, and a pharmaceutically acceptable carrier or diluent, wherein at least 80% (preferably 90%, more preferably 99%) by weight of the salt is crystal form S4.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the present teachings can be formulated with a carrier such as sugar, acacia, tragacanth, or gelatin and glycerine, as tablets, lozenges or pastilles.

For rectal administration, the compounds described herein can be formulated in the form of suppositories containing a conventional suppository base such as cocoa butter.

The disclosure is illustrated by the following examples, which are not intended to be limiting in any way.

EXPERIMENTAL

Abbreviations

| Abbreviation | Solvent | Abbreviation | Solvent |
|---|---|---|---|
| MeOH | Methanol | ACN | Acetonitrile |
| EtOH | Ethanol | MEK | Butanone |
| n-PrOH | 1-Propanol | MCH | Methylcyclohexane |
| IPA | Isopropyl alcohol | MTBE | Methyl tert-butyl ether |
| MIBK | 4-Methyl-2-pentanone | DMSO | Dimethylsulfoxide |
| EA | Ethyl acetate | THF | Tetrahydrofuran |
| FA | Fumaric acid | 2Me-THF | 2-Methyltetrahydrofuran |
| IPAc | Isopropyl acetate | | |

Units

| Full Name | Abbreviation |
|---|---|
| Celsius | C. |
| Degrees | ° |
| Equivalents | eq. |
| Gram | g |
| Hour | h |
| Kelvin | K |
| Liters | L |
| Milligrams | mg |
| Milliliters | mL |
| Minute | min |
| Milliamp | mA |
| Kilovolt | kV |
| In-Process-Control | IPC |
| Relative Humidity | RH |
| Mass Variation over Time Variation | rpm |
| Room temperature | RT |
| Second | sec |
| volume | vol. |
| Volume ratio | v/v |
| Watt | W |
| Weight | wt. |
| Weight Percentage | wt. % |

Analysis Conditions

X-Ray Powder Diffraction (XRPD)

Samples were analyzed on a Panalytical CubiX-Pro X-ray powder diffractometer or a Bruker D8 Advance XRP diffractometer.

Panalytical Conditions: Samples were placed on a silicon zero-return ultra-micro sample holder. The samples were irradiated with copper K-alpha X-rays with the X-ray tube operated at 40 kV/30 mA. The samples were scanned in continuous mode along the range 3 to 45°.

Bruker D8 Advance XRP instrument Parameters: A high-power Cu-target was used operating at 40 kV/40 mA. Lynxeye detector was used with a PSD opening of 2.1°. The samples were scanned along the range 4-40° (2σ) where representative peaks for most of the organic crystalline compounds occur.

Dynamic Vapor Sorption (DVS)

Hygroscopicity measurements were performed by transferring about 10 mg of sample into a DVS instrument and subsequently recording the weight change with respect to the atmospheric humidity at 25° C. using the following parameters:

| | | |
|---|---|---|
| Total gas flow(sccm) | | 200 |
| Oven(° C.) | | 25 |
| Solvent | | Water |
| Method | Preheat | N/A |
| | Dry | N/A |
| | Stage Mode | DMDT |
| | method | Cycle: RH 0%-90%-0% or 50%-90%-50% |
| | | Stage Step: 10% |
| | | Dm/dt criteria: <0.002% sampling rate: 1 min |
| | | minimum duration: 10 min |
| | | maximum duration: 360 min |

Purity by HPLC

The purity of a sample was determined by HPLC. The HPLC operating parameters are listed below:

| | | | |
|---|---|---|---|
| Column details | Agilent Eclipse plus C18 (150 * 4.6 mm, 3.5 μm) PDS-HPLC-104 | | |
| Column temperature | 40° C. | | |
| Mobile phase A | 0.05% TFA in Water | | |
| Mobile phase B | 0.05% TFA in Methanol | | |
| Flow rate | 1 mL/min | | |
| Gradient profile | Time (mins) | % Mobile Phase A | % Mobile Phase B |
| | 0.00 | 70 | 30 |
| | 8.00 | 30 | 70 |
| | 9.00 | 10 | 90 |
| | 10.00 | 10 | 90 |
| | 11.00 | 70 | 30 |
| | 15.00 | 70 | 30 |
| Detector wavelength | 270 nm (for concentration), 330 nm (for assay and purity) | | |
| Injection volume | 2 μL | | |
| Needle wash solvent | Methanol | | |
| Dilution | Water:Methanol (50/50, v/v) | | |

Example 1: Small Scale Crystallization in Acetone Produces Form D but is not Reproducible at Larger Scales Several small scale crystallization experiments in acetone were carried out in which compound (I) and fumaric acid on 2 g scale were dissolved in acetone at 50-60° C. In Experiments 1 and 2, the compound (I) and acid solution were mixed, followed by evaporation to concentrate the solvent and cooling to 0° C. in 2-5 hours. Form D was generated successfully from the crystallization without seeding and from the crystallization with seeding. Both experiments yielded form D, which was stable in a solution for at least 17 hours from the crystallization with and without seeding. In Experiment 3, concentration of the solvent was omitted from the procedure and no solid precipitated from the solution. It was concluded from the experiments that concentration of the solvent was necessary to yield form D (Table 1).

Next, the crystallization procedure in acetone was scaled up to 3.5 g, and the total concentration time was extended to around 10 h. In this experiment, form D converted to form S4 after concentrating for 3 hours.

It was attempted to concentrate the fumaric acid solution before salt formation. After dissolving fumaric acid in acetone, the acid solution was concentrated to 8 volumes, resulting in a suspension of fumaric acid. Then compound (I) was dissolved in acetone (32 volumes) and added to the acid suspension at 55° C. with 1% seed and holding for one hour at 55° C. The solution was cooled to 5° C. and held for 16-17 hours. Form D was generated successfully (Table 2). However, it was found that the form D suspension could be held at 50° C. for less than 2.5 hours before conversion into form S4.

Because of the rapid conversion to form S4 at 50-55° C. in acetone, it was decided to determine the effect of reducing the holding time at 50-55° C. As such, the hold time at 50-55° C. was reduced to 10 minutes for batches of 1 gram and 5 gram scales, after which the temperature was cooled to 0° C. over 1.5 hours and held at that temperature for 16-17 hours. Although form D was obtained in good quality, the yield was lowered to 63% and 65% respectively (Table 3). The experiment was repeated in which the temperature was reduced to 25° C. for 24 hours before cooling to 5° C. This experiment still produced form D in good quality, however, the yield loss was still around 12%. It was also found that further cooling to 5° C. did not help to further reduce the loss (Table 4).

In an attempt to further increase the yield of crystallization, a cold anti-solvent was added during the cooling stage. Methyl t-butyl ether (MTBE) was selected as the anti-solvent, and two experiments were carried out with 1 gram and 5 gram quantities of compound (I). Compound (I) solution in acetone (34 volumes) were combined with fumaric acid suspension in acetone (8 volumes) at 50° C. and 1% seed and held for 0.5 hours. This was followed by the addition of MTBE and cooling to 0° C. over 1.5 hours. The crystallization with the 1 gram sample provided form D, but the 5 gram batch yielded a mixture of D and S4. Neither experiment gave a satisfactory yield (64% and 60%, respectively) (Table 5).

The crystallization procedure was then repeated, lowering the temperature at which compound (I) and fumaric acid were mixed to 25° C. and 35° C. Mixtures of Forms D and S4 were obtained (Table 6).

TABLE 1

Summary of preliminary crystallization experiments in acetone

| ID | Procedure | IPC XRPD After concentration | Slurry 17 h | Slurry 60 h | Wet cake XRPD | Dry cake XRPD |
|---|---|---|---|---|---|---|
| Experiment 1 | Seed 2%, concentration, cooling to 0° C., stir speed 180 rpm | Form D | Form D | Form D | Form D | Form D |
| Experiment 2 | No seed, concentration, cooling to 0° C., stir speed 180 rpm | Form D | Form D | N/A | Form D | Form D |
| Experiment 3 | Seed 2%, no concentration, cooling to 0° C., stir speed 180 rpm | No solid | No solid | No solid | No solid | No solid |

TABLE 2

Scale-up of the evaporation crystallization in acetone

| Procedure | IPC (XRPD) IPC1 | IPC2 | IPC3 | Wet cake XRPD | Dry cake XRPD |
|---|---|---|---|---|---|
| Freebase was dissolved in 32 vol; Acid was dissolved then concentrated to 8 vol; Freebase was added to acid at 55° C. adding 1% seed; | Hold for 1 h at 55° C.: Form D | Cool to 5° C. Form D | Hold for 16-17 h at 5° C.: Form D | Form D | Form D |

TABLE 3

Reduction of the holding time after seeding

| Scale size | Procedure | IPC (XRPD) Cool to 0° C. | 16-17 h at 0° C. | Dry cake XRPD | Purity | Assay | Residual solvent | ML loss | Isolated yield |
|---|---|---|---|---|---|---|---|---|---|
| 1 g scale | Hold at 50° C. for 10 min; cool to 0° C. over 1.5 h | D | D | D | 99.7% | 98.0% | Acetone: 0.269% MTBE 0.010% | ~25% | ~63% |
| 5 g scale | Hold at 50° C. for 10 min; cool to 0° C. over 1.5 h | D | D | D | 99.3% | 99.2% | Acetone: 0.37% MTBE: 0.04% | ~33% | ~65% |

TABLE 4

Optimization of the crystallization yield by holding at 25° C.

| | | IPC (XRPD) | | Dry cake | | | | | |
|---|---|---|---|---|---|---|---|---|---|
| Scale Size. | Procedure | IPC1 | IPC2 | XRPD | Purity | Assay | Residual solvent | ML loss | Yield by solid |
| 4 g scale | 25° C. Hold for 24 h | Hold at 25° C. for 24 h: Form D | Hold at 5° C. for 16 h: Form D | Form D | 99.7% | 97.5% | Acetone 0.29% MTBE 0.02% | 25° C.: ~12% 5° C.: ~12% | ~82% |

TABLE 5

Addition of the cold MTBE during cooling

| | | Dry cake | | | | | |
|---|---|---|---|---|---|---|---|
| Scale Size | Procedure | XRPD | Purity | Assay | Residual solvent | ML loss | Yield by solid |
| 1 g scale | Freebase solution(34 vol); Fuamric acid suspension(8 vol); adding 1% seed; Hold at 50° C. for 0.5 h; add 30 vol MTBE; cooling to 0° C. over 1.5 h | Form D | 99.7% | 98.1% | Acetone 0.217% MTBE 0.026% | ~27% | ~64% |
| 5 g scale | Freebase solution(34 vol); Fuamric acid suspension(8 vol); adding 1% seed; Hold at 50° C. for 0.5 h; add 30 vol MTBE; cooling to 0° C. over 1.5 h | Form D + Form S4 | 99.3% | 98.4% | Acetone 0.37% MTBE 0.06% | ~40% | ~60% |

TABLE 6

Salt formation in acetone at 25° C. and 35° C.

| Freebase | Fumaric acid | Temperature | Dry solid XRPD |
|---|---|---|---|
| 5 vol | 5 vol | 25° C. | Form S4 |
| 5 vol | 20 vol | 25° C. | Form S4 |
| 34 vol | 5 vol | 25° C. | Form D + Form S4 |
| 15 vol | 5 vol | 35° C. | Form D + Form S4 |

Example 2: Crystallization Quality is Dependent on the Starting Material

From the results of Example 1 above, it appeared that salt formation in acetone at 50° C. was the most promising procedure to deliver form D in a reasonable yield. In the proposed procedure, compound (I) acetone solution was initially charged to the fumaric acid acetone suspension at 50° C. resulting in a supersaturated acetone solution. This supersaturated solution was then seeded. The system was held after seeding (before cooling) for no longer than 2 hours; the system was then cooled to 25° C., followed by holding at 25° C. overnight. After filtration, the cake was washed with methyl t-butyl ether and dried at 50° C. under vacuum. This procedure could deliver desirable form D with a yield of >60%. In order to verify the proposed procedure, several experiments were carried out on 4 gram (purity 99.1%) and 9 gram (purity 99.8%) scales. The experiment with the 4 gram batch delivered desirable form D, but the experiment with the 9 gram scale produced form S4. As the scales of two experiments were similar, it was believed the results might depend on the quality of the starting material (Table 7).

In order to study the influence of the quality of the starting material, several experiments were carried out (Table 8) using starting materials of different purities. In Experiment 4, less pure compound (I) was used for the experiment. However, no obvious crystallization was found during the study. In Experiment 5, a batch of compound (I) with high purity was mixed with several batches of less pure material and used as the starting material. No crystallization was observed after seeding. The holding time was extended to 3 hours at 50° C., but a mixture of form D and S4 were generated. In Experiment 6, a mixture of typical pure compound (I) and mother liquor from compound (I) preparation (mother liquor from compound (I) synthesis step) was used as the starting material. Form D was generated and could be maintained for a relatively longer time.

In order to study the effect of the residual solvent in compound (I), several "spiking" experiments were carried out (Table 9). The "spiked" solvents were solvents that were used in the synthesis steps. In addition, compound (I) was amorphous in some batches. In order to study whether the polymorphism of compound (I) might affect the polymorph of the salt, an experiment starting with amorphous compound (I) was carried out. In Experiment 7, 3% MeOH was added to the system, and form D converted to form S4 during holding at 50° C. In Experiment 8, 1% methyl acetate was added to the system, and form D converted to form S4 during holding at 50° C. In Experiment 9, amorphous compound (I) was used as the starting material, and form D converted to form S4 during holding at 50° C.

In summation, an evaporative crystallization procedure was developed to yield form D. However, it was then found that the success of the procedure was highly dependent on the purity and form of the starting material. Thus, starting materials with slightly different minor impurities or purity levels yielded different polymorphs. The success of the crystallization was found to also be dependent on minor variations in crystallization conditions and scale of the crystallization. However, the critical factors which controlled the formation of form D or stable form S4 were not determined.

TABLE 7

Repeatability of the proposed procedure in acetone

| Scale size | Starting material | Procedure | IPC1 | IPC (XRPD) IPC2 | IPC3 | ML loss | Yield by solid |
|---|---|---|---|---|---|---|---|
| 4 g scale | Purity: 99.1% | Proposed procedure | Hold at 25° C. for 2 h: Form D | Hold at 25° C. for 18 h: Form D | Hold at 25° C. for 24 h: Form D | ~12% | ~82% |
| 9 g scale | Purity: 99.8% | Proposed procedure | Hold at 50° C. for 0.5 h: Form D + Form S4 | Hold at 25° C. for 16 h: Mainly S4 | N/A | ~10% | ~87% |

ML: mother liquor.

TABLE 8

Effects of the starting material

| Scale size | Starting material | Procedure | IPC1 | IPC (XRPD) IPC2 | IPC 3 | ML loss | Yield by solid |
|---|---|---|---|---|---|---|---|
| 8 g scale Experiment 4 | Purity: 98.5% | Proposed procedure | No obvious crystallization | | | | |
| 3 g scale Experiment 5 | Purity: 98.02% (mixed batch) | Hold at 50° C. for 3 h | Hold at 50° C. for 1.5 h: Form D + Form S4 | | | N/A | 74% |
| 3 g scale Experiment 6 | Purity: 98.28% (MeOH ML addition) | Proposed procedure | After add compound (I): Form D | Cooling to 25° C.: Form D | Hold at 25° C. for 16 h: Mainly Form D | N/A | 75% |

TABLE 9

Different batches of the starting material

| Scale size/ Experiment ID | Starting material | Procedure | After add compound (I) | IPC (XRPD) Hold at 50° C. for 0.5 h | Hold at 25° C. for 18 h | ML loss | Yield by solid |
|---|---|---|---|---|---|---|---|
| 2.2 g scale Experiment 7 | Purity: 99.91% | Add 2.2 g MeOH | Form D | Form D + Form S4 | Form S4 | 13% | 87% |
| 2.2 g scale Experiment 8 | Purity: 99.91% | Add 1 g Methyl Acetate | Form D | Form D + Form S4 | Form S4 | 6% | 90% |
| 3 g scale Experiment 9 | Amorphous | Proposed procedure | Form D | Form D + Form S4 | Form S4 | 13% | 84% |

Example 3: Large Scale Manufacturing Process Intended for Pure Form D Resulted in a 1:1 Mixture of Forms D and S4

1.05 kg compound (I) was dissolved in 5-10 kg acetone at 55-60° C. with stirring for 30 min to make the compound (I) solution. A solution of 0.32 kg fumaric acid dissolved in 35 kg acetone was slowly added to the compound (I) solution at 60° C. The resulting mixture was concentrated before adding 3.5 g seed crystals comprising form D. The mixture was stirred at 60° C. for 1-2 h. The mixture was then concentrated and cooled to 50° C. in 2 h. Next, 4 kg MTBE was slowly added to the mixture at 50° C. and the resulting mixture was stirred for an additional 1-2 h at the same temperature. The mixture was cooled to 25° C. slowly over a period of 20-25 h. Polymorphic transformation was detected at the end of the cooling process, resulting in a 1:1 mixture of polymorphic forms D and S4. The fumarate salt was then collected, washed twice with 3-4 kg MTBE, filtered and dried at 65-70° C. for 8-24 h. 1.02 kg of a 1:1 mixture of polymorphic forms D and S4 was obtained as the final product.

Example 4: Small Scale Preparation of 1:1 Compound (I) Fumarate Crystal Form S4

A novel small-scale crystallization procedure in the MEK/water/EtOH/MCH solvent system was developed as follows: 0.282 g fumaric acid was dissolved in 5 ml ethanol at 50° C. to make the acid solution. 1.0 g compound (I) was dissolved in 7 ml 2-butanone/water (95/5 volume ratio) at 50° C. to make the compound (I) solution. 20% of the acid solution was charged to the compound (I) solution, 20 mg seed crystals were added to the mixed solution, and then the rest of the acid was added dropwise. The temperature was held at 50° C. for 3 hours, and then cooled to 25° C. in 2.5 hours and held at 25° C. for an additional 17 hours. Next, 22 volume equivalent of methylcyclohexane was added in 2 hours. The temperature was cooled to 5° C. in 30 minutes and held at 5° C. for an additional 3 hours. The sample was filtered and dried at 50° C. under vacuum to obtain the final product, which was confirmed by XRPD as the single crystal form S4. The XRPD pattern for this final product was essentially the same as those shown in FIG. 1 and listed in Table 10 for the final product prepared by using 100 g compound (I) based on the same procedure. Due to its unique XRPD pattern with sharp peaks and a flat baseline, form S4 was believed to be a single crystal form with at least 90% crystalline purity.

To improve product yield, methylcyclohexane needs to be properly added as the anti-solvent. Specifically, when the volume ratios of 2-butanone/water (95/5) to ethanol to methylcyclohexane are 6-7 to 4-5 to 11-22, form S4 with a yield higher than 90% can be consistently obtained (Table 11). Also, the molar ratio between fumaric acid and compound (I) can be fine-tuned to improve the yield, primarily through decreasing product solubility. When the molar ratio of fumaric acid to compound (I) changed from 1.1 to 1.5, the loss in the yield of form S4 decreased from 7% to 3% (Table 12). The molar ratio of 1.3 was later found to perform equally well as 1.5, and thus applied to the crystallization procedure.

The crystallization procedure was concluded to be quite robust from tests under various stressed conditions, including: fumaric acid solution or compound (I) solution each prepared and held at 50° C. for a lengthened period of time (up to 24 hours), fast addition (no more than half an hour) of fumaric acid or methylcyclohexyl anti-solvent, fast cooling (Table 13). Even under these stressed conditions, form S4 was consistently obtained with very high purity; and the yields, while slightly decreased, were still far better than those obtained for form D from the procedures disclosed in the present disclosure (see Examples 1-2) and in U.S. Pat. No. 9,884,855 (see Example 6).

TABLE 10

XRPD of Form S4

| 2θ angle (°) | Relative Intensity (%) |
|---|---|
| 6.6 | 19.0 |
| 9.8 | 52.1 |
| 11.6 | 11.9 |
| 13.0 | 43.5 |
| 16.3 | 100.0 |
| 17.1 | 12.6 |
| 19.5 | 30.4 |
| 21.1 | 84.9 |
| 21.5 | 14.4 |
| 22.0 | 11.0 |
| 22.5 | 40.2 |
| 22.9 | 18.9 |
| 23.9 | 18.9 |
| 24.3 | 10.2 |
| 28.7 | 16.5 |
| 29.4 | 22.9 |
| 30.2 | 17.8 |

TABLE 11

Preliminary crystallization in MEK/water/EtOH (MCH)

| | | XRPD | | Dry cake | | | | |
|---|---|---|---|---|---|---|---|---|
| Scale Size | Solvent system | Right after solid precipitated | Before isolation | Assay | Purity | KF | Residual solvent | Loss |
| 3 g scale | MEK/water (95 v/5 v): 10 vol EtOH: 4-5 vol | S4 | S4 | 99.87% | 99.88% | 0.18% | MEK: 0.03% EtOH: ND | 33% |
| 3 g scale | MEK/water (95 v/5 v): 6-7 vol EtOH: 4-5 vol MCH: 11 vol | S4 | S4 | 98.56% | 99.87% | 0.33% | MEK: 0.055% EtOH: 0.035% MCH: 0.009% | 8% |
| 2 g scale | MEK/water (95 v/5 v): 6-7 vol EtOH: 4-5 vol MCH: 22 vol | S4 | S4 | 98.43% | 99.86% | 0.15% | 0.07% EtOH 0.04% MEK 0.01% MCH | 3% |

TABLE 12

Effects of the amount of acid added

| | | | Dry cake | | | | | |
|---|---|---|---|---|---|---|---|---|
| Scale Size | Mole ratio Fumaric acid/ Compound (I) | Wet cake | Assay | Purity | KF | Residual solvent | Assay of Fumaric acid | ML loss |
| 1 g scale | 1.1 | Form S4 | 99.01% | 99.87% | 0.14% | EtOH: 0.06% MEK: 0.05% MCH: 0.00% | 17.82% | ~7% |

TABLE 12-continued

Effects of the amount of acid added

| Scale Size | Mole ratio Fumaric acid/ Compound (I) | Wet cake | Dry cake | | | | | ML loss |
|---|---|---|---|---|---|---|---|---|
| | | | Assay | Purity | KF | Residual solvent | Assay of Fumaric acid | |
| 1 g scale | 1.5 | Form S4 | 98.48% | 99.85% | 0.14% | EtOH: 0.05% MEK: 0.04% MCH: 0.00% | 17.85% | ~3% |

TABLE 13

Stress tests

| Scale Size | Procedure | IPC (XRPD) After add FA | Wet cake | Dry cake | | | | ML loss | Yield by solid |
|---|---|---|---|---|---|---|---|---|---|
| | | | | Assay | Purity | KF | RS | | |
| 1 g scale | FA EtOH solution stir at 50° C. for 24 h | Form S4 | Form S4 | 97.28% | 99.8% | 0.06% | 0.08% EtOH 0.05% MEK 0.01% MCH | ~5% | 86% |
| 1 g scale | Fast add FA; fast cooling to 25° C.; hold at 5° C. for 72 h | N/A | Form S4 | N/A | 99.8% | 0.09% | 0.12% EtOH 0.08% MEK 0.00% MCH | ~4% | N/A |
| 1 g scale | MCH fast add; fast cooling to 5° C. | Form S4 | Form S4 | 97.59% | 99.9% | 0.05% | 0.07% EtOH 0.06% MEK 0.00% MCH | ~4% | ~82% |
| 1 g scale | compound (I) solution (Purity: 99.6%) stir at 50° C. for 20 h(Purity: 99.0%) | Form S4 | Form S4 | 98.74% | 99.8% | 0.07% | 0.06% EtOH 0.04% MEK 0.01% MCH | ~4% | ~80% |

Example 5: Large Scale Manufacturing Process for Form S4

Figure 2:
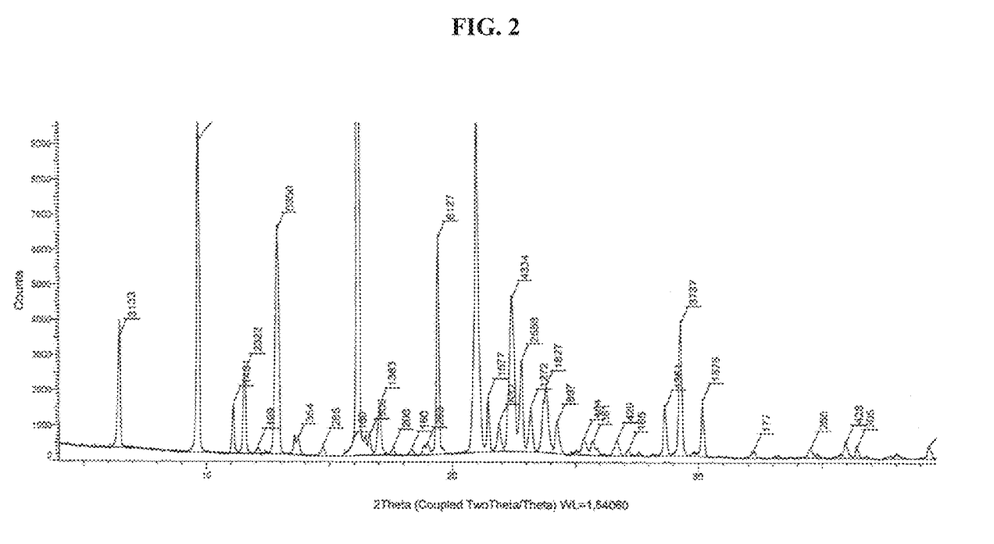
FIG. 2 depicts an X-ray powder diffraction pattern (XRPD) for crystal form S4 of 1:1 fumarate acid salt of compound (I) from the large-scale production in Example 5.

To manufacture form S4 in a large scale, 17.0 kg compound (I) was dissolved in 90 kg 2-butanone/water (95/5 volume ratio) at 45-55° C. with stirring for 1-4 h to form a compound (I) solution. 4.3 kg fumaric acid was dissolved in 74 kg EtOH at 45-55° C. with stirring for 1-4 h to form an acid solution. A portion of the acid solution was charged to the compound (I) solution at 45-55° C., and stirred at 45-55° C. for 0.5-4 h. Seed crystals comprising form S4 were added to the mixed solution. The seeded mixture was stirred at 45-55° C. for 2-6 h, and then the remaining acid solution was added. The resulting mixture was stirred at 45-55° C. for 3-12 h, and then cooled to 20-30° C. over a period of 5-12 h. Next, 284 kg methylcyclohexane was added slowly over a period of 6-8 h. After the addition, the mixture was stirred at 20-30° C. for 3-12 h, then cooled to 0-10° C. over a period of 3-12 h, and held at 0-10° C. with stirring for additional 6-8 h. The desired salt was then collected, washed twice with 16 kg MCH, filtered, and dried at 50° C. for 8-24 h to obtain 17.96 kg final product, which was confirmed by XRPD as the single crystal form S4 (see FIG. 2). Due to its unique XRPD pattern with sharp peaks and a flat baseline, form S4 was believed to be a single crystal form with at least 90% crystalline purity.

Example 6: Hygroscopicity and Solubility Tests

Based on the DVS measurements described previously, form S4 exhibited low hygroscopicity between 0-80% RH with only 0.41% weight gain at 80% RH, slightly lower than that of form D with 0.56% weight gain at 80% RH.

Multiple tests were performed to evaluate the solubility behavior of form S4 relative to that of form D. Intrinsic dissolution rates at pH 2 showed similar results for form S4 (429.3 µg/cm$^2$-min) and form D (440.4 µg/cm$^2$-min). Also, equilibrium solubilities were measured in various bio-relevant media at ambient temperature. Form S4 showed high equilibrium solubility (2.52 mg/ml) in the fasted state simulating gastric fluid (FaSSGF) and low equilibrium solubility (0.05 mg/ml) in the fasted state simulating intestinal fluid (FaSSIF), similar to those observed for form D (2.08 and 0.08 mg/ml, respectively).

According to the FDA's guidance, in vitro dissolution testing of a drug substance in its oral dosage forms can be properly designed to establish an In Vivo-In Vitro Correlation (IVIVC), i.e., the correlation between an in-vitro property of a dosage form and an in-vivo response. With this guidance, two batches of fumarate containing crystal forms D and S4 were used to prepare tablets, to evaluate any impact on performance of the drug product. Each of the two batches of fumarate and excipients were individually sieved before weighing. The desired weight of each component was then transferred into a shaker mixer and blended. Tableting for the two batches was then performed using a single punch tablet press.

The performance of these tablets was then evaluated using a properly validated dissolution test method. The results showed both batches of tablets have very similar dissolution profiles: the final mean concentration at 60 min for all batches reached 94% (see Table 14). These data show that drug products made of crystal form S4 exhibit equivalent performance as form D with respect to in vitro dissolution testing, inferring bioequivalence as suggested by the FDA's guidance.

TABLE 14

In-vitro dissolution testing for forms S4 and D in their respective oral dosage forms

| Test Description | Polymorphic Form Specification | Time | Form D | | | Form S4 | | |
|---|---|---|---|---|---|---|---|---|
| | | | Min | Max | Mean | Min | Max | Mean |
| Dissolution | Report Mean Results | 15 | 61% | 64% | 63% | 74% | 77% | 76% |
| | | 30 | 81% | 86% | 83% | 89% | 91% | 90% |
| | | 60 | 92% | 98% | 94% | 93% | 95% | 94% |

Example 7: Pharmacokinetic Analysis

During the clinical development of compound (I), two batches of the fumarate salt each containing either polymorphic form D or form S4 were used to prepare tablets, according to Current Good Manufacturing Practice (cGMP) regulations. These are referred to as form D and form S4 tablets in the section below.

Methods:
Drug Administration, Blood Collection and Plasma Preparation

Patients were dosed in clinical trials approved by Health Canada and the Research Ethics Board of the Hospital administering the drug. Eight patients were administered the form S4 tablets, six at a dose level of 48 mg and two at a dose level of 160 mg. 64 patients were administered the form D tablets at doses ranging from 3-160 mg.

Blood was collected for analysis prior to dosing and 2, 4, and 6 h after dosing. Briefly, using standard phlebotomy procedures, approximately 6 mL of blood was collected into a $K_3$EDTA blood collection tube and then inverted 8-10 times to mix. The sample was then centrifuged at 1,000 g for 10-15 min at approximately 5° C. The plasma fraction of the blood was removed using a disposable pipette, transferred to a new tube, frozen at −70° C. and subsequently shipped on dry ice for analysis.

Human Plasma Analysis

Levels of compound (I) were measured in plasma using a method validated in accordance to all applicable USFDA, OECD and MHLW regulations and the USFDA Guidance for Industry: Bioanalytical Method Validation May 2001. Briefly, human plasma samples containing compound (I) with compound (I) $^{13}C_6$ as the internal standard and K3EDTA as the anticoagulant were prepared by liquid/liquid extraction. After evaporation of the extraction solvent, the sample extracts were reconstituted and analyzed by reversed-phase HPLC using a Waters Atlantis dC18. The mobile phase was nebulized using heated nitrogen in a Z-spray source/interface set to electrospray positive ionization. The ionized compounds were detected using MS/MS. Experimental samples were compared with standard curve samples made up using reference standard material to determine compound concentrations. Pharmacokinetic parameters were determined using the Excel add in "PK Functions"

Results

Figure 3:
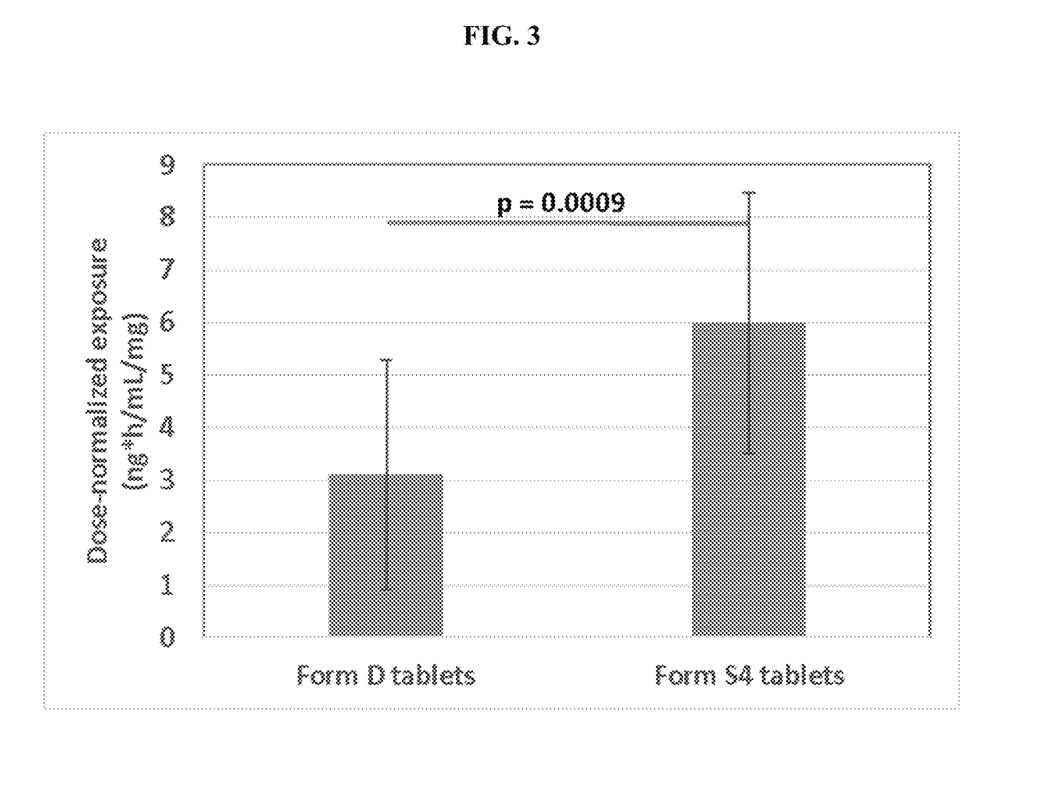
FIG. 3 shows dose-normalized exposure following dosing with form D and form S4.

To compare the doses at different dose levels, the exposure ($AUC_{0-6\,h}$ value) in ng*h/mL was divided by the dose administered (mg). The results are plotted in FIG. 3. The average dose-normalized exposure following dosing with form D tablets was 3.11±2.19 ng*h/mL/mg. The average dose-normalized exposure following dosing with form S4 was 5.99±2.48 ng*h/mL/mg. The p value for significance, calculated using a two-tailed t-test, was 0.0009.

CONCLUSION

Dosing with tablets containing form S4 results in higher exposure levels in patients than dosing with tablets containing form D. In the data presented, the average fold increase in exposure following dosing with form S4 tablets compared to form D tablets is 5.99/3.11=1.9-fold.

What is claimed is:

1. A fumarate salt of compound (I) represented by the following structural formula:

Compound (I)

wherein the molar ratio between compound (I) and fumaric acid is 1:1, and the fumarate salt comprises crystal form S4, characterized by an X-ray powder diffraction pattern which comprises peaks at 6.6°, 9.8°, 16.3°, 21.1°, 28.7°, and 30.2°±0.2 in 2θ.

2. The fumarate salt of claim 1, wherein the fumarate salt comprises crystal form S4, characterized by an X-ray powder diffraction pattern which comprises peaks at 6.6°, 9.8°, 16.3°, 21.1°, 28.7°, 29.4°, and 30.2°±0.2 in 2θ.

3. The fumarate salt of claim 1, wherein the fumarate salt comprises crystal form S4, characterized by an X-ray powder diffraction pattern which comprises peaks at 6.6°, 9.8°, 13.0°, 16.3°, 19.5°, 21.1°, 22.5°, 28.7°, 29.4°, and 30.2°±0.2 in 2θ.

4. The fumarate salt of claim 1, wherein the fumarate salt comprises crystal form S4, characterized by an X-ray powder diffraction pattern which comprises peaks at 6.6°, 9.8°, 13.0°, 16.3°, 19.5°, 21.1°, 22.5°, 22.9°, 23.9°, 28.7°, 29.4°, and 30.2°±0.2 in 2θ.

5. The fumarate salt of claim 1, wherein the fumarate salt comprises crystal form S4, characterized by an X-ray powder diffraction pattern which comprises peaks at 6.6°, 9.8°, 11.6°, 13.0°, 16.3°, 17.1°, 19.5°, 21.1°, 21.5°, 22.0°, 22.5°, 22.9°, 23.9°, 24.3°, 28.7°, 29.4°, and 30.2°±0.2 in 2θ.

6. The fumarate salt of claim 1, wherein the fumarate salt comprises crystal form S4, characterized by an X-ray powder diffraction pattern similar to FIG. 1.

7. The fumarate salt of claim 1, wherein at least 90% by weight of the salt is in a single crystal form, form S4.

8. The fumarate salt of claim 1, wherein at least 99% by weight of the salt is in a single crystal form, form S4.

9. The fumarate salt of claim 1, wherein the fumarate salt contains less than 30% by weight crystal form D, characterized by an X-ray powder diffraction pattern which comprises peaks at 9.6°, 12.8°, 16.0°, 16.9°, 21.2°, and 22.0°±0.2 in 2θ.

10. The fumarate salt of claim 1, wherein the fumarate salt contains less than 10% by weight crystal form D, characterized by an X-ray powder diffraction pattern which comprises peaks at 9.6°, 12.8°, 16.0°, 16.9°, 21.2°, and 22.0°±0.2 in 2θ.

11. A pharmaceutical composition comprising the fumarate salt of claim 1, and a pharmaceutically acceptable carrier or diluent.

12. A method of preparing crystal form S4 of a fumarate salt of compound (I) of claim 1:

(I)

comprising dissolving fumaric acid and compound (I) in a dissolution solvent comprising 2-butanone, water, and ethanol to form a crystallization solution, and then precipitating the crystal form S4 from the crystallization solution, wherein:
the molar ratio between compound (I) and fumaric acid in the dissolution solvent is 1:1 to 1:1.3; and the molar ratio between compound (I) and fumaric acid in the fumarate salt is 1:1.

13. The method of claim 12, comprising dissolving fumaric acid and compound (I) in the dissolution solvent at an elevated temperature, and precipitating the crystal form S4 from the crystallization solution by way of cooling and/or adding methylcyclohexane with cooling.

14. The method of claim 12, comprising the following steps:

(i) dissolving compound (I) in a mixture of 2-butanone and water at an elevated temperature to form a compound (I) solution;

(ii) dissolving fumaric acid in ethanol at an elevated temperature to form a fumaric acid solution;

(iii) adding the fumaric acid solution to the compound (I) solution at an elevated temperature to form the crystallization solution;

(iv) optionally adding seed crystals at an elevated temperature to the crystallization solution; and (v) reducing the temperature of the crystallization solution to precipitate the S4 crystal form.

15. The method of claim 14, wherein the volume ratio between 2-butanone and water is between 80:20 and 98:2, the elevated temperature is between 45° C. and 55° C.; and the reduced temperature is between 20° C. and 30° C.

16. The method of claim 14, wherein the volume ratio between 2-butanone and water is between 90:10 and 98:2, the elevated temperature is between 45° C. and 55° C.; and the reduced temperature is between 20° C. and 30° C.

17. The method of claim 15, further comprising adding methylcyclohexane at a reduced temperature to the crystallization solution to precipitate the S4 crystal form, wherein the volume ratios of 2-butanone/water to ethanol to methylcyclohexane are 6-7 to 4-5 to 11-22.

18. The method of claim 17, wherein the temperature of the crystallization solution is further reduced to precipitate the S4 crystal form.

19. The method of claim 18, wherein the further reduced temperature is between 0° C. and 10° C.

20. A method of treating a subject with a cancer, comprising administering to the subject an effective amount of the fumerate salt of claim 1, wherein the cancer is selected from the group consisting of lung cancer, brain cancer, ovarian cancer, melanoma, prostate cancer, colon cancer, and breast cancer.

21. The method of claim 20, wherein the cancer is selected from the group consisting of lung cancer, breast cancer and colon cancer.

22. The method of claim 20, wherein the cancer is breast cancer.

23. The method of claim 22, wherein the cancer is triple negative breast cancer.

24. The method of claim 23, wherein the triple negative breast cancer is unresectable or metastatic.

25. A method of treating a subject with pancreatic cancer, comprising administering to the subject an effective amount of the fumarate salt of claim 1, or a pharmaceutical composition thereof.

* * * * *